United States Patent
Dotan et al.

(10) Patent No.: US 7,572,592 B2
(45) Date of Patent: *Aug. 11, 2009

(54) METHOD FOR DIAGNOSING MULTIPLE SCLEROSIS

(75) Inventors: Nir Dotan, Lod (IL); Avinoam Dukler, Lod (IL); Mikael Scwartz, Lod (IL)

(73) Assignee: Glycominds Ltd (IL)

( * ) Notice: Subject to any disclaimer, the term of this patent is extended or adjusted under 35 U.S.C. 154(b) by 304 days.

This patent is subject to a terminal disclaimer.

(21) Appl. No.: 11/047,124

(22) Filed: Jan. 31, 2005

(65) Prior Publication Data

US 2006/0172338 A1 Aug. 3, 2006

(51) Int. Cl.
*G01N 33/53* (2006.01)
(52) U.S. Cl. .................................................. 435/7.1
(58) Field of Classification Search ........................ None
See application file for complete search history.

(56) References Cited

U.S. PATENT DOCUMENTS

| 6,972,172 B2 | 12/2005 | Dukler et al. | ................ 435/6 |
| 2004/0077023 A1* | 4/2004 | Dotan et al. | ................ 435/7.2 |

FOREIGN PATENT DOCUMENTS

| WO | WO 00/49412 | 8/2000 |
| WO | WO 01/14881 A1 | 3/2001 |
| WO | WO 02/18950 A1 | 3/2002 |
| WO | WO 02/064556 A2 | 8/2002 |
| WO | WO 03/000733 A2 | 1/2003 |
| WO | WO 2004/015420 A1 | 2/2004 |

OTHER PUBLICATIONS

Schwarz, M., et al. J. Neurol. Sci. 2006; 244:59-68.*
Bao *J. Chromatogr. B.*, 699(1+2):463-480 (1997).
Berger et al. *N. Engl. J. Med.*, 349:139-145 (2003).
Bozzaro et al. *Cell Differentiation*, 17:83-94 (1985).
Brex et al. *N. Engl. J. Med.*, 346(3):158-164 (2002).
Carotenuto et al. *J. Med. Chem.*, 44:2378-2381 (2001).
Comi et al. *Lancet*, 357:1576-1582 (2001).
Holme et al. *Carbohydr. Res.*, 8:43-55 (1968).
Hou et al. *J. Immunol.*, 170:4373-4379 (2003).
Jacobs et al. *Ann. Neurol.*, 41(3):392-398 (1997).
Jacobs et al. *N. Engl. J. Med.*, 343(13):898-904 (2000).
Kurtzke *Neurol.*, 33(11):1444-1452 (1983).
Matsuda et al. *Mol. Immun.*, 24(5):421-425 (1987).
McDonald et al. *Ann. Neurol.*, 50(1):121-127 (2001).
O'Riordan et al. *Brain*, 121:495-503 (1998).
Papini et al. *Proceedings of the 10th International Congress of Immunology*, Monduzzi Editore, pp. 1239-1244 (1998).
Poser et al. *Ann. Neurol.*, 13(3):227-231 (1983).
Rongen et al. *J. Immunol. Meth.*, 204(2):105-133 (1997).
Saveliev et al. *Immun. Letters*, 86:291-297 (2003).
Schmalzing et al. *Electrophoresis*, 18(12-13):2184-2193 (1997).
Schwarz et al. *Glycobiol.*, 13(11):749-754 (2003).
Self et al. *Curr. Opin. Biotechnol.*, 7:60-65 (1996).
Weinshenker et al. *Brain*, 112(part VI):1419-1428 (1989).
Zhan et al. *Biochem. Biophys. Res. Commun.*, 308(1):12-22 (2003).

* cited by examiner

*Primary Examiner*—G. R Ewoldt
(74) *Attorney, Agent, or Firm*—Mintz, Levin, Cohn, Ferris, Glovsky and Popeo P.C.; Ingrid A. Beattie, Esq.

(57) ABSTRACT

Disclosed is a method for diagnosing multiple sclerosis and more particularly to a method for diagnosing multiple sclerosis by measuring levels of antibodies to glycans in a biological sample.

9 Claims, 1 Drawing Sheet

METHOD FOR DIAGNOSING MULTIPLE SCLEROSIS

FIELD OF THE INVENTION

The invention relates generally to a method and reagents for diagnosing, and assessing the prognosis of, multiple sclerosis and more particularly to a method and reagents for diagnosing, and assessing the prognosis of, multiple sclerosis by measuring levels of antibodies to glycans in a biological sample.

BACKGROUND OF THE INVENTION

Multiple sclerosis (MS) is a chronic autoimmune inflammatory disease of the central nervous system. It is a common cause of persistent disability in young adults. In patients suffering from MS, the immune system destroys the myelin sheet of axons in the brain and the spinal chord, causing a variety of neurological pathologies. In the most common form of MS, Relapsing-Remitting, episodes of acute worsening of neurological function (exacerbations, attacks) are followed by partial or complete recovery periods (remissions) that are free of disease progression (stable). It has been reported that ninety percent of patients with MS initially present with a clinically isolated syndrome because of an inflammatory demyelinating lesion in the optic nerve, brain stem, or spinal cord. About thirty percent of those patients with a clinically isolated syndrome progress to clinically definite MS within 12 months of presentation. The subsequent progression of the disease can vary significantly from patient to patient. The progression can range from a benign course to a classic relapsing—remitting, chronic progressive, or rare fulminant course. A method for diagnosing MS that facilitates early MS diagnosis and prediction of disease activity (Benign, Moderate and Malignant) would be valuable for both managing the disease and providing counsel for the patient. For example, patients diagnosed early with active course of MS could be offered disease modifying treatments that have recently been shown to be beneficial in early MS.

Current methods for assessment and tracking progress of MS are based on assessment and scoring of patients' function in attacks and accumulated disabilities during the attacks. One assessment used to assess MS is the Expanded Disability Status Scale (EDSS). However, EDSS score system measures the outcome and does not have predict for the progression of the disease. In addition, EDSS scoring can be variable because it is based on a subjective assessment of patient function. Methods for diagnosis can also include tracking brain lesions by Magnetic Resonance Imaging (MRI) or testing Cerebrospinal Fluid (CSF) for Oligo-Clonal Banding (OCB). MRI is a physical method for assessment of brain lesions and is used widely for MS diagnosis. However, it has only very long term predictive value. In addition, the correlation between MRI results and disease activity is poor. Thus, MRI can not be used for short term projections of disease activity or disease management.

Cerebrospinal puncture is an unpleasant invasive procedure that is not suitable for routine use or prognosis. In addition, both methods assess damage only after it has occurred; neither method can predict the onset of attacks or silent, sub-clinical lesions. A further disadvantage in testing for OCB in CSF and MRI as a way to diagnose MS is that a negative OCB or MRI will not preclude the existence of MS.

Most patients with MS initially present with a clinically isolated syndrome (CIS). Despite the fact that MS will develop in up to 80% of these patients, the course of the disease is unpredictable at its onset. The disease may remain inactive for many years before the appearance of a second clinical relapse or new lesions on MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions.

There is a need for a simple serological assay that predicts whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary. This assay would be also useful in helping the diagnosis of MS.

There is also a need for a method that uses objectively assessed markers for diagnosing MS and for predicting disease activity, the onset of attacks or silent lesions in patients suffering from MS.

SUMMARY OF THE INVENTION

The invention is based in part on the discovery that MS patients have higher serum levels of IgM antibodies that bind the glycan structures Glc($\alpha$1,2)Glc($\alpha$) or Glc($\alpha$1,3)Glc($\alpha$) or Glc($\alpha$1,6)Glc($\alpha$) as compared to the serum levels of these antibodies in individuals with other neurological diseases (chronic, inflammatory or non-inflammatory). The levels of IgM anti Glc($\alpha$1,2)Glc($\alpha$) or Glc($\alpha$1,3)Glc($\alpha$) or Glc($\alpha$1,6) Glc($\alpha$) in serum can act as a staging and prognostic marker for the activity of the disease. Levels of the antibodies can also be used to decide on treatment and to track the efficacy of treatment.

Measuring the levels of these antibodies in the blood of MS suspected patients facilitates quick and cost effective early diagnosis of MS patients, disease activity prediction and early prescribing of disease modifying drugs. Monitoring of the levels of those antibodies in the blood of defined MS patients also allows for quick and cost effective monitoring of the effects of prescribed drugs, and early detection of attacks or sub-clinical silent lesions, enabling better treatment.

Among the additional advantages of the invention are that the existence of MS in patients can be determined at an earlier stage of the disease, when its symptoms may resemble many other MS-like diseases or when the symptoms are still not sufficient to finally define the patient as having MS. Early diagnosis allows physicians to treat MS earlier in the course of the disease, thereby minimizing or preventing the damage caused by the destruction of myelin and disabilities brought about by this destruction. In addition, the methods disclosed herein enable physicians to follow MS patients regularly in order to assess the disease activity, to monitor therapy, and change treatment once signs for coming attacks appear. For example, an increase in biomarkers indicative of an MS attack may warrant administration to the patient of methylpredisone, which is a general anti inflammatory agent commonly administered during attacks.

In one aspect, the invention features a method of diagnosing, or assessing the prognosis of, multiple sclerosis in a subject. The method includes providing a test sample from a subject and detecting in the test sample at least one biomarker that is an antibody that binds specifically to a glycan structure. The antibody can be, e.g., anti-Glc($\alpha$1,2)Glc($\alpha$) antibody or anti-Glc($\alpha$1,3)Glc(($\alpha$) antibody or anti-Glc($\alpha$1,6)Glc($\alpha$) antibody. The levels of antibody or antibodies in the test sample are compared to a control sample, which is derived from one or more individuals who have multiple sclerosis symptoms and have a known multiple sclerosis status, or from an individual or individuals who do not show multiple sclerosis symptoms. MS status can include, e.g., exacerbations, attacks, remissions, benign, moderate, malignant and stable stages of the disease.

In various embodiments, at least 1, 2 or 3 of these antibodies are detected.

In some embodiments, the method further comprises detecting one or more additional antibodies. The antibody can be, e.g., an anti α-Glc antibody (including an anti α-Glc IgM antibody), an anti-Glc(α1,4)Glc(α) antibody (including an anti-Glc(α1,4)Glc(α) IgM antibody), an anti α-GlcNAc antibody (including an anti α-GlcNAc IgM antibody), an anti β-GlcNAc antibody, an anti-Glc(α1,4)Glc(β) antibody an anti β-Glc antibody, an anti β-Gal antibody, an anti-Glc(α1, 4)Glc(β1,4)Glc(β) antibody, an anti-GlcNAc(β,1,4)GlcNAc (β) antibody, an anti α-L-Araf antibody, an anti α-L-Rha antibody, an anti-Gal (β1,3)[GlcNAc(β1,6)]GalNAc(α) antibody, an anti-Gal(β1,4)GlcNAc(α) antibody, an anti-Gal(β1, 3)GalNAc(α), an anti-Gal(β,1-3)GlcNAc(β), an anti β-GlcA antibody or an anti α-Xyl antibody. In various embodiments, at least 2, 3, 4, 5, 6, 7, 8, 9, 10, 11, 12, 13, 14, 15, 16, 17 or 18 of these additional antibodies are detected.

In some embodiments, the control sample consists essentially of a population of one or more individuals that do not show symptoms of a multiple sclerosis and do not have multiple sclerosis. In other embodiments, the control sample consists essentially of a population who do show symptoms of a multiple sclerosis and do have multiple sclerosis. In other embodiments, the control sample consists essentially of a population of one or more individuals with neurological diseases other then multiple sclerosis. In other embodiments, the control sample consists essentially of a population of one or more individuals with autoimmune diseases other then multiple sclerosis.

The presence of MS in the control sample can be determined using techniques known in the art, e.g., Clinical neurological examination, or an Expanded Disability Status Scale (EDSS) assessment, Magnetic Resonance Imaging (MRI) assessment, or testing for OCB in the CSF or combination of some or all of the techniques.

The test sample can be, e.g., a biological fluid. Examples of biological fluids include, e.g., whole blood, serum, plasma, spinal cord fluid, urine, tears or saliva.

The subject can be either a female or a male.

The antibody detected can be, e.g., an IgM type or an IgA type or an IgG antibody.

In some embodiments, the type of multiple sclerosis detected is early multiple sclerosis.

Also provided by the invention is a method of diagnosing a multiple sclerosis exacerbation in a subject. The method includes providing a test sample from a subject and detecting an anti-Glc(α1,2)Glc(α) antibody or anti-Glc(α1,3)Glc(α) antibody or anti-Glc(α1,6)Glc(α) antibody in the test sample. The levels of the antibody in the test sample are compared to a control sample, which is derived from one or more individuals whose multiple sclerosis status is known.

In some embodiments, the control sample consists essentially of a population of one or more individuals that do not show symptoms of a multiple sclerosis exacerbation and whose multiple sclerosis status is in remission. A multiple sclerosis exacerbation is diagnosed in the subject if more anti-Glc(α1,2)Glc(α) antibody or anti-Glc(α1,3)Glc(α) antibody or anti-Glc(α1,6)Glc(α) antibody is present in the test sample than in the control sample. In other embodiments, the control sample consists essentially of a population of one or more individuals that show symptoms of a multiple sclerosis exacerbation, and a multiple sclerosis exacerbation is diagnosed in the subject if levels of anti-Glc(α1,2)Glc(α) antibody or anti-Glc(α1,3)Glc(α) antibody or anti-Glc(α1,6)Glc (α) antibody are present in similar amounts in the test sample and the control sample.

The test sample can be, e.g., a biological fluid. Examples of biological fluids include, e.g., whole blood, serum, plasma, spinal cord fluid, urine, tears or saliva.

The subject can be either a female or a male.

The antibody detected can be, e.g., an IgM type, an IgA or an IgG type antibody.

In some embodiments, the diagnosis is an early diagnosis of multiple sclerosis exacerbation.

In some embodiments, the subject has been treated with an MS therapeutic agent, e.g., interferon beta or glitamerer acetate administered subcutaneously.

Also within the invention is method for assessing multiple sclerosis disease activity in a subject. The method includes providing a test sample from a subject and determining whether the test sample contains an anti-Glc(α1,2)Glc(α) antibody or anti-Glc(α1,3)Glc(α) antibody or anti-Glc((α1, 6)Glc(α) antibody. The amount of antibody in the test sample is compared to the amount of the antibody in the control sample, which is derived from one or more individuals whose multiple sclerosis disease activity is known.

In some embodiments, the control sample consists essentially of a population of one or more individuals whose multiple sclerosis disease activity is defined by Expanded Disability Status Scale (EDSS), changes in an EDSS score, frequency of relapses or a Magnetic Resonance Imaging (MRI) assessment.

The test sample can be, e.g., a biological fluid. Examples of biological fluids include, e.g., whole blood, serum, plasma, spinal cord fluid, urine, tears or saliva. If desired, the method may further include selecting a therapeutic agent for treating multiple sclerosis by selecting a therapeutic agent and dosage regimen based on the relative levels of the antibody or antibodies in the test sample and the control sample.

In some embodiments, higher levels of antibodies in the test sample relative to the control sample indicate selection of a therapeutic agent and dosage regimen that is subcutaneous administration of interferon beta (BETAFERON®, AVONEX®, REBIF®) or subcutaneous administration of glitamerer acetate (COPAXONE®).

The subject can be either a female or a male.

In a further aspect, the invention provides a method of selecting a therapeutic agent for treating multiple sclerosis. The method includes providing a test sample from a subject diagnosed with, or at risk for, multiple sclerosis and determining whether the test sample contains anti-Glc(α1,2)Glc (α) antibody or anti-Glc(α1,3)Glc(a) antibody or anti-Glc (α1,6)Glc(α) antibody. Levels of the antibody in the test sample to are compared to levels of antibody in a control sample consisting essentially of one or more individuals whose multiple sclerosis disease activity is known. A therapeutic agent and dosage regimen is selected based on the relative levels of the antibody in the subject sample and the control sample.

In some embodiments, the method further includes determining whether the test sample contains anti-Glc(α1,2)Glc (α) antibody or anti-Glc(α1,3)Glc(α) antibody or anti-Glc (α1,6)Glc(α) antibody and comparing the levels of anti-Glc (α1,2)Glc(α) antibody or anti-Glc(α1,3)Glc(α) antibody or anti-Glc(α1,6)Glc(α) antibody in the test sample to levels of antibody in a control sample consisting essentially of one or more individuals whose multiple sclerosis disease severity is known.

In some embodiments, the control sample consists essentially of one or more individuals whose status is no multiple sclerosis or stable multiple sclerosis.

In a further aspect, the invention provides a method to predict whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary.

The method includes providing a test sample from a subject diagnosed with, or at risk for, multiple sclerosis and determining whether the test sample contains anti-Glc($\alpha$1,2)Glc ($\alpha$) antibody or anti-Glc($\alpha$1,3)Glc($\alpha$) antibody or anti-Glc(($\alpha$1,6)Glc($\alpha$) antibody. Levels of the antibody in the test sample are compared to levels of antibody in a control sample consisting essentially of one or more individuals whose multiple sclerosis disease activity and course is known. A therapeutic agent and dosage regimen is selected based on the relative levels of the antibody in the subject sample and the control sample.

Also provided by the invention is a kit for diagnosing and predicting disease activity associated with multiple sclerosis. The kit includes a first reagent that specifically detects anti-Glc($\alpha$1,2)Glc($\alpha$) antibody or anti-Glc($\alpha$1,3)Glc($\alpha$) antibody or anti-Glc($\alpha$1,6)Glc($\alpha$) antibody, and a second reagent that specifically detects specifically detects a second antibody selected from the group consisting of an anti $\alpha$-Glc antibody (including an anti $\alpha$-Glc IgM antibody), an anti-Glc($\alpha$1,4)Glc($\alpha$) antibody (including an anti-Glc($\alpha$1,4)Glc($\alpha$) IgM antibody), an anti $\alpha$-GlcNAc antibody (including an anti $\alpha$-GlcNAc IgM antibody), an anti $\beta$-GlcNAc antibody, an anti-Glc($\alpha$1,4)Glc($\beta$) antibody an anti $\beta$-Glc antibody, an anti $\beta$-Gal antibody, an anti-Glc($\beta$1,4)Glc($\beta$1,4)Glc($\beta$) antibody, an anti-GlcNAc($\beta$1,4)GlcNAc(p) antibody, an anti $\alpha$-L-Araf antibody, an anti $\alpha$-L-Rha antibody, an anti-Gal ($\beta$1,3)[GlcNAc($\beta$1,6)]GalNAc($\alpha$) antibody, an anti-Gal($\beta$1,4)GlcNAc($\alpha$) antibody, an anti-Gal($\beta$1,3)GalNAc($\alpha$), an anti-Gal($\beta$,1-3)GlcNAc($\beta$), an anti $\beta$-GlcA antibody and an anti $\alpha$-Xyl antibody. The kit may include one or all reagents, and directions for using the kit. The kit optionally includes a reagent that specifically detects an IgM type antibody.

Also within the invention are substrates that include reagents that specifically detect the antibodies disclosed herein, e.g., anti-Glc($\alpha$1,2)Glc($\alpha$) antibody or anti-Glc(($\alpha$1,3)Glc($\alpha$) antibody or anti-Glc($\alpha$1,6)Glc($\alpha$) antibody. The invention also includes reagents that specifically detect antibodies used in combination with the antibodies disclosed above, e.g., an anti $\alpha$-Glc antibody (including an anti $\alpha$-Glc IgM antibody), an anti-Glc($\alpha$1,4)Glc($\alpha$) antibody (including an anti-Glc($\alpha$1,4)Glc($\alpha$) IgM antibody), an anti $\alpha$-GlcNAc antibody (including an anti $\alpha$-GlcNAc IgM antibody), an anti $\beta$-GlcNAc antibody, an anti-Glc($\beta$1,4)Glc($\beta$) antibody an anti $\beta$-Glc antibody, an anti $\beta$-Gal antibody, an anti-Glc($\beta$1,4)Glc($\beta$1,4)Glc($\beta$) antibody, an anti-GlcNAc($\beta$1,4)GlcNAc ($\beta$) antibody, an anti $\alpha$-L-Araf antibody, an anti $\alpha$-L-Rha antibody, an anti-Gal ($\beta$1,3)[GlcNAc($\beta$1,6)]GalNAc($\alpha$) antibody, an anti-Gal($\beta$1,4)GlcNAc($\alpha$) antibody, an anti-Gal($\beta$1,3)GalNAc($\alpha$), an anti-Gal($\beta$1-3)GlcNAc($\beta$), an anti $\beta$-GlcA antibody or an anti $\alpha$-Xyl antibody. The substrate can be, e.g., planar. In a further aspect, the reagents may be connected to a substrate via a linker.

Also within the invention are reagents for diagnosing and predicting disease activity associated with multiple sclerosis, that specifically detects anti-Glc($\alpha$1,2)Glc($\alpha$) antibody or anti-Glc($\alpha$1,3)Glc($\alpha$) antibody or anti-Glc($\alpha$1,6)Glc($\alpha$) antibody or all. In a further aspect, the reagents may be connected to a substrate via a linker. The substrate may be a bead particles or a planer substrate.

In some embodiments, the reagents that are used to specifically bind and detect those anti glycans antibodies are the specific glycan structures. In other embodiments, the reagents are other molecules or macromolecules that include the specific glycan structure. For example, the anti-Glc($\alpha$1,2)Glc($\alpha$) antibody can be detected using a polymer of glucose units connected with one or more Glc($\alpha$1,2)Glc($\alpha$) glycosidic bonds. Thus, the glycan itself can be used for detecting the corresponding antibody or antibodies, as can any carbohydrate, peptide, protein, or any other molecular structure that includes the glycan.

In some embodiments, the reagents that are used to specifically bind and detect the anti glycans antibodies of the invention are peptides that mimic the carbohydrate antigens of the invention. The peptides can be used to identify specific anti glycan antibodies.

In some embodiment peptides that mimics the specific carbohydrates of this invention can be used for identification of the specific anti glycan antibodies. Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
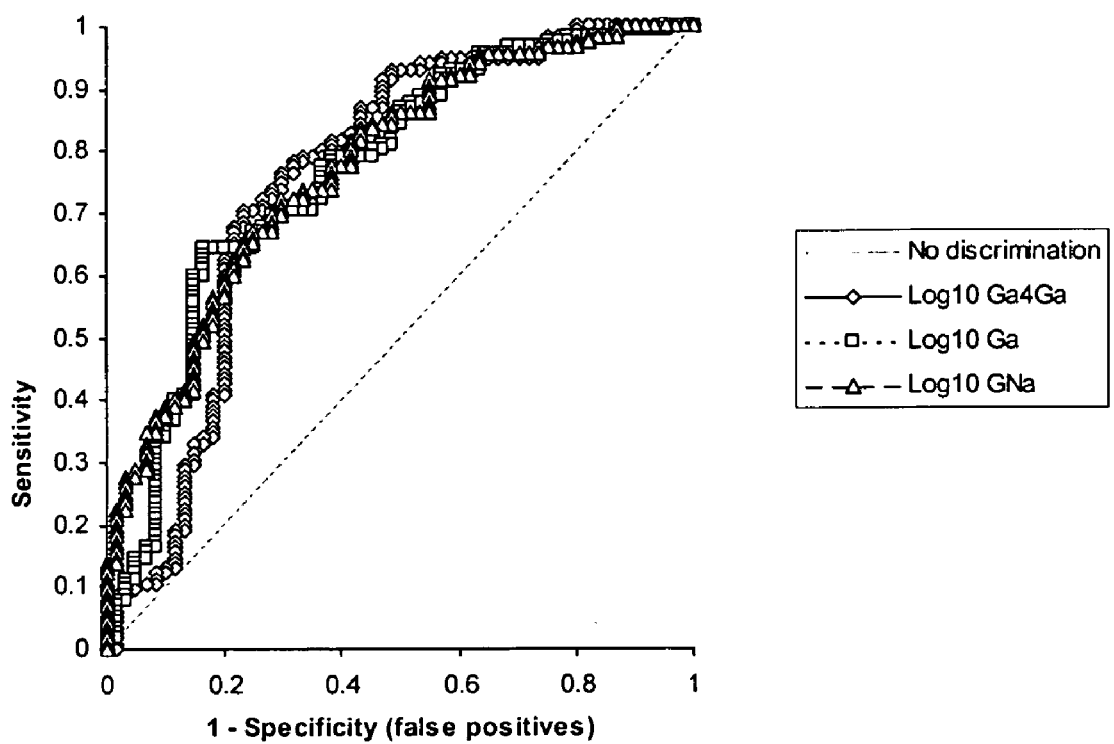
FIG. 1 is a graph showing Receiver Operator Characteristic (ROC) curves for differentiation between MS and OND patients using level of IgM antibodies against Glc($\alpha$1,2)Glc ($\alpha$)-(Ga2Ga), Glc($\alpha$1,3)Glc($\alpha$)-Ga3Ga, Glc(($\alpha$1,6)Glc($\alpha$)-Ga6Ga, Glc($\alpha$1,4)Glc($\alpha$)-Ga4Ga, $\alpha$-Glc-Ga, $\alpha$-GlcNAc-GNa.
Figure 1:
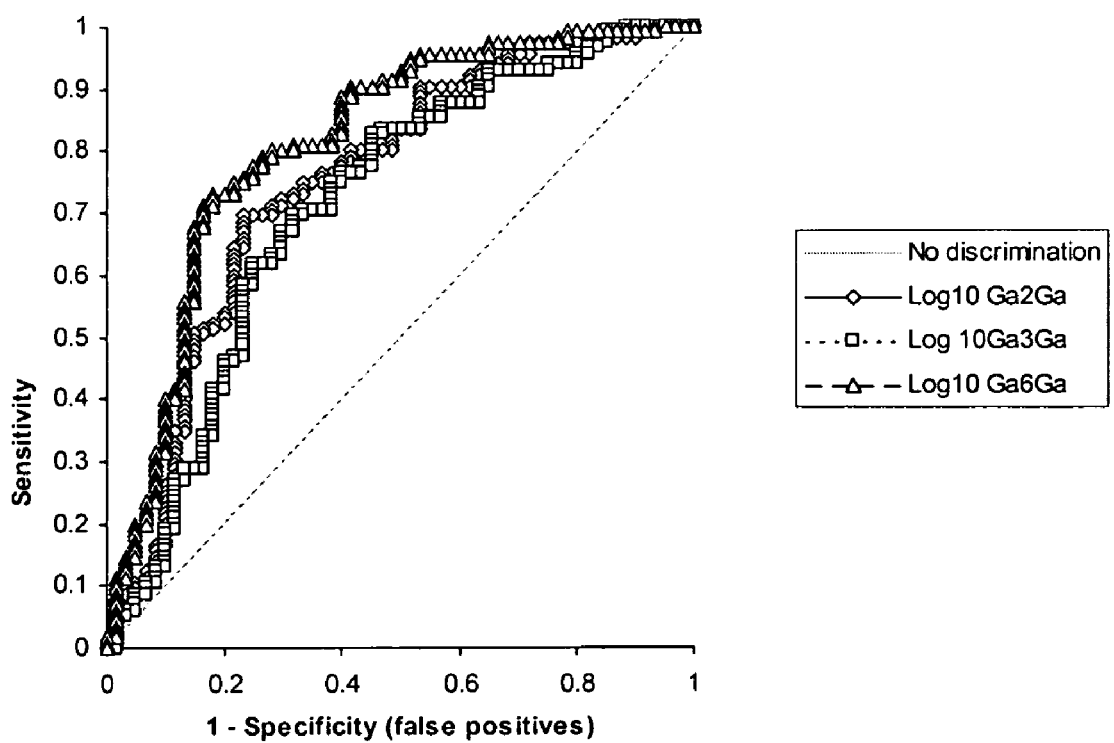

The methods provided herein allow for early diagnosis of initial and recurring multiple sclerosis, as well as prediction of disease activity (benign, moderate and malignant), using objectively assessed biomarker levels.

A patient with acute worsening of neurological function initially has to be diagnosed as a defined MS patient before being eligible for treatment with disease modifying drugs. The physician will have to determine if the patient has MS like symptoms (such as Younger stroke, Lupus, Vitamin B-12 deficiency, Anti phospholipid syndrome, Severe Migraine) or if they actually have MS. The patient will have to experience a second acute worsening of neurological function (attack) before being diagnosed as a MS patient and be able to start chronic treatment with a MS therapeutic agent such as interferon beta or glatiramer acetate.

Currently, physicians are using MRI for the identification of the existence of brain lesions and/or the testing of Cerebrospinal Fluid (CSF) for Oligo Clonal Banding (OCB). If MRI gives a clear result regarding the existence of brain lesions or the presence of OCB in the CSF, the physician may start treatment immediately in order to prevent silent brain lesions. A diagnosis of full MS diagnosis is currently made only after the second attack or the appearance new MRI finding with dissemination in time and space. In case MRI does not give a clear result or there are no OCB in the patients CSF, no MS is diagnosed and treatment is delayed until following a second attack (McDonald et al., Ann Neurol. 50:121-27, 2001).

Most patients with MS initially present with a clinically isolated syndrome (CIS). Despite the fact that MS will develop in up to 80% of these patients, the course of the disease is unpredictable at its onset. The disease may remain inactive for many years before the appearance of a second clinical relapse or new lesions on MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions. This invention provides a simple serological assay to predict whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary. This assay is also useful for helping diagnosing MS.

The methods disclosed herein can be performed by extracting blood from a patient with acute worsening of neurological function and suspected to have MS or an already defined RRMS patient. The method can identify the existence of MS and to predict the up coming course of the diseases by measuring anti-Glc($\alpha$1,2)Glc($\alpha$) antibody or anti-Glc($\alpha$1,3)Glc ($\alpha$) antibody or anti-Glc($\alpha$1,6)Glc($\alpha$) antibody levels. If the level of at least one of these antibodies is significantly higher then the average level of these antibodies in sera of healthy individuals, patients with neurological diseases other then MS, or patients with autoimmune diseases other then MS, the patient is diagnosed as an MS patient without the need to wait for a second attack or for further MRI findings. In addition, the quick diagnosis allows for treatment to begin immediately.

Screening the patient's blood and determining the level of biomarkers disclosed herein, anti-Glc($\alpha$1,2)Glc($\alpha$) antibody or anti-Glc($\alpha$1,3)Glc($\alpha$) antibody or anti-Glc($\alpha$1,6)Glc($\alpha$) antibody, allows for accurate monitoring of therapy. For example, one first line of treatment for MS is interferon $\beta$ (e.g., INF$\beta$-1a and INF$\beta$-1b). The current evaluation of effectiveness and required dosage of the drug is based on continued monitoring of several clinical scores. Currently, the EDSS score and its change over time (e.g., by comparing the difference in the EDSS every 3-6 months) is the main clinical parameter for disease management. An important component of the assessment is the level of fatigue and depression experienced by the patient. The fatigue and or depression can be a symptom of MS, as an autoimmune disease, or a side effect from the usage of interferon beta. Identifying the cause of the fatigue is important for managing the treatment. For example, if the fatigue is a result of a side effect of the interferon, the physician will consider lowering the dosage or even exchanging it for another drug. However, if the fatigue is due to the MS symptoms, the physician will have to consider increasing the drug dosage. Significant decreases in antibody levels indicate that the patient is responding well to the given drug.

Currently there is no way to predict the onset of attacks and sub-clinical silent lesions in MS patients. MRI and clinical evaluation of the patients can only reveal damage that has already occurred. Periodical measurement of the level of a few anti glycan antibodies (for example, anti-Glc($\alpha$1,2)Glc ($\alpha$) antibody or anti-Glc($\alpha$1,3)Glc($\alpha$) antibody or anti-Glc ($\alpha$1,6)Glc($\alpha$) antibody) in the patient's blood according to the method described herein allows for physicians to predict the upcoming disease activity (e.g. frequency of clinical attacks and appearance of sub clinical MRI silent lesions) based upon an increase in levels of these antibodies.

All the glycan structures that are discussed in this disclosure, unless mentioned otherwise are connected to in the indicated anomericity $\alpha$ or $\beta$ through linker to solid phase.

In some embodiment peptides that mimics the specific glycans of this invention can be used for identification of the specific anti glycan antibodies. Those peptide that mimics carbohydrate can be identifies for example from screening a filamentous phage-displayed random peptide library (Zhan et al., Biochem Biophys Res Commun. 308:19-22, 2003; Hou et al., J Immunol. 170:4373-79, 2003).

Most patients with Multiple Sclerosis (MS) initially present with a clinically isolated syndrome (CIS). Despite the fact that clinically definite MS will develop in up to 80% of these patients, the course of the disease is unpredictable at its onset. The disease may remain inactive for many years before the appearance of a second clinical relapse or new lesions on MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions.

The invention provides a simple serological assay that may be used to predict whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary.

The invention additionally provides a simple serological test for the definite confirmation of MS and of the level of the risk in individuals presenting a primary acute demyelinating event. Ninety percent of patients with MS initially present with a clinically isolated syndrome due to an inflammatory demyelinating lesion in the optic nerve, brain stem, or spinal cord (O'Riordan et al., Brain 121: 495-503, 1998). Thirty percent of these patients with clinically isolated syndrome will have progression to definite multiple sclerosis within 12 month after presentation (Brex et al., N. Engl. J. Med. 346: 158-164, 2002; O'Riordan et al., Brain 121: 495-503, 1998; Jacobs et al., Ann. Neurol. 41:392-98, 1997), but no more than 80% of patients with a clinically primary event will develop clinically definite MS (Weinshenker et al., Brain 112:1419-28, 1989). Thus, it is desirable to unambiguously confirm and stage MS prior to commencing treatment with disease modifying drugs.

The methods can be used to determine whether a particular treatment MS treatment regimen is warranted for a particular patient. Patients at high risk for rapid progression to definite MS can be offered disease-modifying treatments that have recently been shown to be beneficial in early multiple sclerosis (Comi et al., Lancet 351:1576-82, 2001; Jacobs et al., N. Engl. J. Med. 343:898-904, 2000). On the other hand, for patients at low risk, and who have a chance of remaining relapse free for several years after an initial demyelinating event, immunomodulatory therapy might be postponed until necessary. Thus, an advantage of the invention is better disease management at the early days of the disease.

The presence of antibodies to Glc($\alpha$1,2)Glc($\alpha$), Glc($\alpha$1,3)Glc($\alpha$) and/or Glc($\alpha$1,6)Glc($\alpha$) can be combined with other diagnostic tests for diagnosing multiple sclerosis. One such test is the MS-associated antibodies disclosed in WO 2004/015420, the contents of which are incorporated by reference in their entirety. These antibodies include, e.g., an anti $\alpha$-Glc antibody (including an anti $\alpha$-Glc IgM antibody), an anti-Glc($\alpha$1,4)Glc($\alpha$) antibody (including an anti-Glc($\alpha$1,4)Glc($\alpha$) IgM antibody), an anti $\alpha$-GlcNAc antibody (including an anti $\alpha$-GlcNAc IgM antibody), an anti $\beta$-GlcNAc antibody, an anti-Glc($\alpha$1,4)Glc($\beta$) antibody an anti $\beta$-Glc antibody, an anti $\beta$-Gal antibody, an anti-Glc($\beta$1,4)Glc($\beta$1,4)Glc($\beta$) antibody, an anti-GlcNAc($\beta$,1,4)GlcNAc($\beta$) antibody, an anti $\alpha$-L-Araf antibody, an anti $\alpha$-L-Rha antibody, an anti-Gal($\beta$1,3)[GlcNAc($\beta$1,6)]GalNAc($\alpha$) antibody, an anti-Gal($\beta$1,4)GlcNAc($\alpha$) antibody, an anti-Gal($\beta$1,3)GalNAc($\alpha$), an anti-Gal($\beta$,1-3)GlcNAc($\beta$), an anti $\beta$-GlcA antibody or an anti $\alpha$-Xyl antibody.

The methods are typically performed using reagents that specifically bind to the anti-glycan antibodies. The reagents can be, e.g., the specific glycan structures. Alternatively, the reagents can be other molecules or macromolecules that include the specific glycan structure. For example, the Glc($\alpha$1,2)Glc($\alpha$) antibody can be detected using a polysaccharide that includes a polymer with one or more Glc($\alpha$1,2)Glc($\alpha$) linkages. Thus, the glycan itself can be used for detecting the corresponding antibody or antibodies, as can any carbohydrate, peptide, protein, or any other molecular structure that includes the glycan.

If desired, peptides that mimic carbohydrate antigens can be used in the methods and compositions described herein. The peptides can be used to identify specific anti glycan antibodies. Peptides which mimic structures recognized by antiglycan antibodies can be identified using methods known in the art, e.g., by screening a filamentous phage-displayed random peptide library (Zhan et al., Biochem Biophys Res Commun. 308:19-22, 2003; Hou et al., J Immunol. 17:4373-79, 2003).

Glycan antigens used to identify various anti-glycan antibodies can be obtained from a variety of other sources so long as the antigen is capable of binding specifically to the given anti-glycan antibody. Binding to anti-glycan antibodies can be performed using variety of other immunoassay formats known in the art, including competitive and non-competitive immunoassay formats can also be used (Self and Cook, Curr. Opin. Biotechnol. 7:60-65 (1996), which is incorporated by reference). Other assays include immunoassays, such as enzyme-linked immunosorbent assays (ELISAs). An enzyme such as horseradish peroxidase (HRP), alkaline phosphatase (AP), $\beta$-galactosidase or urease can be linked to a secondary antibody selective for a primary anti-glycan antibody of interest. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a $\beta$-galactosidase detection system can be used with the chromogenic substrate o-nitrophenyl-a$\beta$-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab')$_2$ anti-human IgG-alkaline phosphatase, for example, can be purchased from Jackson Immuno-Research (West Grove, Pa.);

Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used (Rongen et al., J. Immunol. Methods 204:105-133 (1997)).

A radioimmunoassay can also be used for determining whether a sample is positive for a glycan antibody, or for determining the level of anti-glycan antibodies in a sample. A radioimmunoassay using, for example, an $^{125}$Iodine-labeled secondary antibody (Harlow and Lane, Antibodies A Laboratory Manual Cold Spring Harbor Laboratory: New York, 1988, which is incorporated herein by reference) is encompassed within the invention.

A secondary antibody may alternatively be labeled with a chemiluminescent marker. Such a chemiluminescent secondary antibody is convenient for sensitive, non-radioactive detection of anti-glycan antibodies and can be obtained commercially from various sources such as Amersham Lifesciences, Inc. (Arlington Heights, Ill.).

A detectable reagent may also be labeled with a fluorochrome. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of $^{125}$Iodine; or a fluorometer to detect fluorescence in the presence of light of a certain wavelength. For detection of enzyme-linked reagents, a quantitative analysis of the amount of anti-glycan antibodies can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Other methods include, e.g., flow cytometry (including bead based immunoassays), and phage display technology for expressing a recombinant antigen specific for an anti-glycan antibody. Phage particles expressing the antigen specific for a desired anti-glycan antibody can be anchored, if desired, to a multiwell plate using an antibody such as an anti phage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

The invention will be illustrated in the following non-limiting examples.

EXAMPLE 1

Recruitment of Patients

One hundred and fifteen (115) Outpatients aged 18-55 years with clinically definite and laboratory-supported MS, according to the Poser criteria (Poser et al., Ann Neurol 13, 227-231, 1883), were eligible for the study. Inclusion criteria for patients with RRMS were a history of at least two clearly identified and documented relapses in the 2 years prior to study entry, and being ambulant, defined by Kurtzke's expanded disability status scale (EDSS) (Kurtzke, Neurology 33, 1444-1452, 1983) of 0-6.5. Relapse was defined as the appearance or reappearance of one or more neurological abnormalities that persisted for at least 24 h, and which had been preceded by at least 30 days of stable or improved neurological state. Exclusion criteria were corticosteroids treatment in the preceding 3 months, previous immunosuppressive therapy with cytotoxic activity or lymphoid irradiation, as well as pregnancy or lactation. Signed informed consent was obtained from patients, and the study was approved by the Ethical Committee of the Lady Davis, Carmel Medical Center, Israel and by the Ethical Committee of Sourasky Medical Center, Tel Aviv, Israel.

Sera of 60 patients affected by other neurological disease (OND) were obtained from Genomics Collaborative, MA, USA, or obtained under informed consent from patients admitted to the Neuroimmunology Unit, Carmel Medical Center, Israel The blood samples were collected in evacuated silicon-coated tubes containing gel for the separation of sera from the blood clot (Estar Technologies, Israel). After coagulation of the blood, serum was separated by centrifugation, collected and kept frozen at $-25°$ C. until use. The laboratory evaluations were conducted in a blind manner in relation to the clinical findings.

Glycan Array

All serum samples were tested using GlycoChip®. The glycans were covalently bound to the surface through a linker, as previously described (Schwarz et al., Glycobiology 13, 749-754, 2003; Dukler and Dotan, WIPO, Vol. WO2002IL0000101, Glycominds Ltd., 2002). Briefly, an oligomer of 1,8-diamino-3,6-dioxaoctan (Sigma, St. Louis, Mo.) was synthesized and coupled to the solid support. Consequently, pNP-saccharide conjugates were reduced by sodium dithionite to pAP-saccharide derivatives and reacted with cyanochloride (Sigma)-activated linker. The following p-nitrophenyl glycans derivatives were spotted on the slides: Glc($\alpha$1,2)Glc($\alpha$), Glc($\alpha$1,3)Glc($\alpha$), Glc($\alpha$1,6)Glc($\alpha$), Glc($\alpha$1,4)Glc($\alpha$), $\alpha$-Glc, and $\alpha$-GlcNAc. The glycans were printed in 6 sub arrays on each slide, 4 spots for each glycan per sub array.

Fluorescent Assay for Specific Glycan-Binding Antibodies using Glass Slide GlycoChip®

An adhesive silicon superstructure attached to the slide after the printing enables to apply 6 different serum samples on each slide simultaneously, 4 patient samples and high and low plasma controls.

Serum samples (diluted 1:80 in TBST containing 1% BSA) were incubated for 1 h on the slides. After washing in TNTT buffer (20 mM Tris-HCl pH 7.2, 2 M NaCl, 0.05% Tween-20, 0.05% Triton X-100) labeling reagents were incubated on the glass slides in a Tecan HS-4800 hybridization system. Biotinylated goat anti-human IgM (1:500) and Alexa-488-labeled streptavidin (1:150; Molecular Probes, OR, USA) were incubated sequentially with washings in between for 1 h at $32°$ C. in the light-protected and temperature-controlled environment of the hybridization system. Slides were scanned using an Axon 4100 array scanner controlled by GenPix (Axon, Calif., USA). Images were analyzed using ArrayPro Analyzer 4.5.1.48 (Media Cybernetics, CA, USA).

Higher Levels of Anti-Glc($\alpha$1,2)Glc($\alpha$), Glc($\alpha$1,3)Glc($\alpha$), and Glc($\alpha$1,6)Glc($\alpha$) IgM Antibodies are Found in Sera of MS Patients vs OND Patients The level of all anti-glycan IgM antibodies tested was significantly higher in MS patients vs. patients with other neurological diseases. Descriptive statistics for anti-glycan IgM antibody levels in 115 multiple sclerosis patients and 60 patients with other neurological diseases are shown in Table 1. The RFU signals were Log10 transformed for achieving normal distribution. The Receiver Operator Characteristic (ROC) curve for differentiation between MS and OND patients is shown in FIG. 1. The results show that all the glycans can differentiate between MS patients and OND patients with 90% specificity and 40-60% sensitivity. Using cutoff values for 90% specificity, it was determined for each of the patients whether the patient was positive (above cutoff) or negative (below cutoff) for each of the antigens tested.

TABLE 1

| | Mean Log10(RFU), (SD) | |
|---|---|---|
| Sugar Antigen | MS | OND |
| Glc($\alpha$1, 2)Glc($\alpha$) | 0.51 (0.19) | 0.32 (0.21) * |
| Glc($\alpha$1, 3)Glc($\alpha$) | 0.45 (0.20) | 0.31 (0.23) * |
| Glc($\alpha$1, 6)Glc($\alpha$) | 0.48 (0.21) | 0.20 (0.23) * |
| Glc($\alpha$1, 4)Glc($\alpha$) | 0.52 (0.20) | 0.32 (0.25) * |
| $\alpha$-Glc | 0.37 (0.18) | 0.17 (0.20) * |
| $\alpha$-GlcNAc | 0.61 (0.25) | 0.33 (0.24) * |

SD, standard deviation;
MS, multiple sclerosis;
OND, other neurological diseases,
RFU, relative fluorescence units.
* $p < 0.000001$ versus MS Levels of anti-glycan antibodies Glc($\alpha$1,4)Glc($\alpha$)-Ga4Ga, $\alpha$-Glc-Ga, $\alpha$-GlcNAc-GNa, Glc($\alpha$1,2)Glc($\alpha$)-Ga2Ga, Glc($\alpha$1,3)Glc($\alpha$)-Ga3Ga, Glc($\alpha$1,6)Glc($\alpha$)-Ga6Ga were determined for each patient. The results are shown in Table 2. Gray patterned cells in Table represent antibodies level above cutoff for 90% specificity. The results show that that there are MS patients who are positive to one or more of Glc($\alpha$1,2)Glc($\alpha$), Glc($\alpha$1,3)Glc($\alpha$), or Glc($\alpha$1,6)Glc($\alpha$) and are not positive for Glc($\alpha$1,4)Glc($\alpha$), $\alpha$-Glc, or $\alpha$-GlcNAc. For example, patient 5138 is positive only for anti Glc($\alpha$1,2)Glc($\alpha$), patients 5414 and 5415 are positive only for anti Glc($\alpha$1,3)Glc($\alpha$) and patient 5446 is positive only for anti Glc($\alpha$1,6)Glc($\alpha$), those patients can be diagnosed only by using only the relevant antigen. Thus, each antigen has a unique specificity contribution for more accurate diagnosis of MS. These results show that anti-Glc($\alpha$1,2)Glc($\alpha$), Glc($\alpha$1,3)Glc($\alpha$), and Glc($\alpha$1,6) Glc($\alpha$) IgM antibodies are found at higher levels in MS patients vs. OND patients. Therefore, these antibodies are useful in the diagnosis of MS patients either by alone or in combination with other antigens.

TABLE 2

| Patient I.D | Disease | Ga4Ga | Ga | GNa | Ga2Ga | Ga3Ga | Ga6-Ga |
|---|---|---|---|---|---|---|---|
| 302 | MS | 2.09 | 1.48 | 1.22 | 2.01 | 2.27 | 2.98 |
| 303 | MS | 1.47 | 1.26 | 3.02 | 2.43 | 3.40 | 1.45 |
| 308 | MS | 4.70 | 3.73 | 5.35 | 5.68 | 2.98 | 4.26 |
| 309 | MS | 2.06 | 1.65 | 1.64 | 3.41 | 1.98 | 1.79 |
| 312 | MS | 1.80 | 1.34 | 1.38 | 3.70 | 1.69 | 1.59 |
| 313 | MS | 5.47 | 3.46 | 3.03 | 4.60 | 6.18 | 4.55 |
| 314 | MS | 4.30 | 2.61 | 6.18 | 6.74 | 4.54 | 4.02 |
| 316 | MS | 3.30 | 3.12 | 8.39 | 3.27 | 2.61 | 2.39 |
| 318 | MS | 3.57 | 2.99 | 3.41 | 2.12 | 2.52 | 5.70 |
| 321 | MS | 2.24 | 2.98 | 5.35 | 4.49 | 3.26 | 2.86 |
| 322 | MS | 4.15 | 2.78 | 2.74 | 3.03 | 2.77 | 2.72 |
| 323 | MS | 2.20 | 1.61 | 4.46 | 3.34 | 2.62 | 4.61 |
| 324 | MS | 4.45 | 2.46 | 7.09 | 3.95 | 3.90 | 2.47 |
| 326 | MS | 3.11 | 3.61 | 4.93 | 11.21 | 3.22 | 7.06 |
| 328 | MS | 5.33 | 2.50 | 4.32 | 1.90 | 2.95 | 3.43 |
| 5086 | MS | 2.70 | 1.76 | 6.60 | 3.47 | 3.23 | 3.31 |
| 5089 | MS | 2.70 | 2.48 | 10.78 | 3.58 | 2.59 | 2.70 |
| 5090 | MS | 4.88 | 2.54 | 4.72 | 3.05 | 3.64 | 3.21 |
| 5093 | MS | 3.36 | 3.13 | 4.30 | 6.70 | 2.58 | 3.97 |
| 5098 | MS | 3.15 | 1.46 | 12.01 | 2.55 | 2.50 | 2.21 |
| 5103 | MS | 9.16 | 4.41 | 13.14 | 8.18 | 5.78 | 6.95 |
| 5106 | MS | 11.15 | 3.57 | 11.36 | 4.26 | 7.68 | 4.17 |
| 5110 | MS | 1.93 | 1.39 | 2.13 | 1.98 | 1.78 | 2.52 |
| 5111 | MS | 4.39 | 2.37 | 3.22 | 4.82 | 3.11 | 4.58 |
| 5113 | MS | 1.89 | 1.44 | 2.94 | 3.13 | 1.97 | 1.69 |
| 5119 | MS | 2.37 | 2.12 | 4.09 | 2.27 | 3.04 | 3.06 |
| 5120 | MS |  | 2.48 |  |  |  |  |
| 5121 | MS | 4.81 | 1.90 |  | 3.32 |  |  |
| 5126 | MS | 3.77 | 1.97 |  | 2.12 | 3.72 | 2.93 |
| 5129 | MS |  | 2.27 | 4.43 |  |  |  |
| 5130 | MS | 2.97 |  | 3.96 | 1.62 | 1.87 | 1.38 |
| 5137 | MS | 3.23 | 2.44 |  |  | 2.30 | 2.62 |
| 5138 | MS | 1.94 | 2.20 | 3.51 |  | 1.88 | 2.66 |
| 5139 | MS | 2.04 | 1.35 | 3.62 | 1.23 | 2.81 | 1.69 |
| 5145 | MS | 1.35 | 0.76 | 1.24 | 1.34 | 1.27 | 0.90 |
| 5158 | MS | 2.04 | 2.21 | 1.98 | 1.69 | 1.75 | 2.15 |
| 5159 | MS | 4.80 |  | 2.96 | 2.96 | 2.77 |  |
| 5163 | MS | 4.17 |  |  | 3.73 | 2.71 |  |
| 5174 | MS | 3.83 | 2.66 | 3.99 | 3.18 | 2.25 |  |
| 5175 | MS | 1.35 | 1.19 | 2.11 | 1.73 | 1.62 | 1.03 |
| 5176 | MS | 3.41 |  |  | 2.69 | 2.07 | 2.78 |
| 5177 | MS |  | 2.58 | 3.42 |  |  | 2.91 |
| 5204 | MS | 2.59 | 1.29 | 2.07 | 2.01 | 1.32 | 2.22 |
| 5207 | MS | 4.49 | 2.49 | 2.81 | 2.17 | 2.40 | 2.84 |
| 5208 | MS | 4.97 |  |  | 3.06 | 2.48 |  |
| 5211 | MS | 4.58 | 1.43 | 3.81 | 2.78 | 1.99 | 1.25 |
| 5212 | MS | 2.02 | 1.70 | 4.15 | 2.54 | 2.23 | 2.42 |
| 5213 | MS | 2.30 | 2.41 | 3.72 | 2.05 | 2.29 | 3.02 |
| 5214 | MS | 3.39 |  |  | 3.23 | 2.64 | 3.12 |
| 5215 | MS | 4.01 |  | 3.99 | 3.02 | 2.43 |  |
| 5216 | MS | 9.81 | 2.35 | 2.43 | 3.12 | 2.94 | 3.75 |
| 5217 | MS | 3.91 | 3.00 | 6.34 | 3.11 | 2.15 | 3.01 |
| 5219 | MS | 2.04 | 2.76 | 2.35 | 4.28 | 1.42 | 1.60 |
| 5230 | MS | 5.49 | 4.02 | 4.30 | 5.11 | 3.19 | 4.20 |
| 5231 | MS | 2.74 | 1.98 | 4.12 | 5.17 | 3.69 | 2.94 |
| 5232 | MS | 4.81 | 3.77 | 12.05 | 4.40 | 11.63 | 7.49 |
| 5240 | MS | 4.10 | 2.30 | 5.05 | 3.90 | 3.32 | 3.18 |
| 5240 | MS | 4.10 | 2.30 | 5.05 | 3.90 | 3.32 | 3.18 |
| 5241 | MS | 2.89 | 1.68 | 7.68 | 6.25 | 4.50 | 3.50 |
| 5242 | MS | 5.52 | 3.08 | 6.14 | 4.15 | 2.69 | 4.11 |
| 5246 | MS | 2.40 | 4.76 | 2.91 | 1.92 | 2.12 | 5.87 |
| 5248 | MS | 1.69 | 1.01 | 2.44 | 2.40 | 2.37 | 1.34 |
| 5249 | MS | 2.99 | 2.15 | 7.17 | 3.79 | 2.76 | 2.66 |
| 5251 | MS | 1.89 | 1.23 | 3.63 | 2.37 | 2.81 | 1.47 |
| 5254 | MS | 2.42 | 2.35 | 2.73 | 1.91 | 1.68 | 1.69 |
| 5255 | MS | 8.92 | 1.53 | 2.97 | 2.76 | 2.84 | 3.31 |
| 5410 | MS | 2.18 | 2.93 | 2.65 | 1.16 | 1.38 | 3.17 |
| 5411 | MS | 1.92 | 1.42 | 8.82 | 1.90 | 1.69 | 4.32 |
| 5412 | MS | 2.63 | 1.72 | 2.08 | 2.02 | 2.17 | 2.97 |
| 5413 | MS | 7.06 | 3.84 | 2.93 | 3.49 | 3.79 | 5.62 |
| 5414 | MS | 2.51 | 1.50 | 2.69 | 4.00 | 3.95 | 2.13 |
| 5415 | MS | 3.67 | 0.91 | 1.33 | 2.33 | 5.02 | 2.59 |
| 5416 | MS | 4.39 | 3.81 | 2.42 | 1.66 | 1.76 | 7.06 |
| 5417 | MS | 5.30 | 6.53 | 17.28 | 4.61 | 4.08 | 7.07 |
| 5418 | MS | 3.50 | 3.04 | 3.26 | 3.05 | 2.56 | 2.42 |
| 5420 | MS | 2.88 | 2.28 | 3.69 | 3.73 | 5.83 | 3.28 |
| 5423 | MS | 2.65 | 1.72 | 2.25 | 4.14 | 2.19 | 2.43 |
| 5424 | MS | 3.01 | 2.20 | 2.23 | 2.26 | 2.53 | 2.04 |
| 5428 | MS | 2.97 | 2.38 | 4.86 | 2.78 | 2.78 | 2.61 |
| 5429 | MS | 3.89 | 2.49 | 4.18 | 8.13 | 6.00 | 5.87 |
| 5430 | MS | 3.12 | 2.31 | 3.23 | 4.16 | 10.76 | 2.28 |
| 5436 | MS | 6.39 | 3.49 | 4.33 | 3.10 | 2.15 | 3.95 |
| 5438 | MS | 2.31 | 2.18 | 2.55 | 2.92 | 3.52 | 1.63 |
| 5441 | MS | 2.28 | 1.83 | 4.69 | 7.07 | 2.82 | 2.37 |
| 5443 | MS | 1.98 | 1.44 | 3.39 | 1.96 | 1.65 | 1.72 |
| 5444 | MS | 9.93 | 4.45 | 10.92 | 7.19 | 10.55 | 7.15 |
| 5446 | MS | 2.29 | 1.66 | 2.89 | 3.43 | 2.89 | 3.87 |
| 5447 | MS | 1.54 | 1.79 | 1.66 | 4.00 | 2.27 | 1.03 |
| 5449 | MS | 6.02 | 2.59 | 8.69 | 5.17 | 4.51 | 4.27 |
| 5450 | MS | 1.46 | 1.12 | 1.64 | 1.55 | 1.25 | 1.41 |
| 5452 | MS | 1.51 | 1.03 | 1.46 | 1.98 | 1.60 | 2.18 |
| 5455 | MS | 3.42 | 3.15 | 2.39 | 1.68 | 1.32 | 1.64 |
| 5456 | MS | 3.69 | 2.42 | 8.09 | 2.16 | 1.15 | 1.99 |
| 5457 | MS | 7.33 | 3.88 | 6.72 | 6.80 | 6.62 | 9.37 |
| 5458 | MS | 2.70 | 1.46 | 3.07 | 4.00 | 2.04 | 1.58 |
| 5460 | MS | 2.96 | 2.39 | 11.87 | 2.98 | 2.00 | 2.91 |
| 5461 | MS | 2.54 | 1.69 | 2.14 | 3.67 | 2.49 | 2.53 |
| 5462 | MS | 2.66 | 1.54 | 2.64 | 3.60 | 2.11 | 1.75 |
| 5463 | MS | 5.56 | 5.11 | 2.69 | 2.81 | 2.02 | 6.63 |
| 5464 | MS | 2.87 | 4.94 | 4.60 | 3.35 | 2.90 | 4.17 |
| 5465 | MS | 3.30 | 2.28 | 4.12 | 4.35 | 2.91 | 2.31 |
| 5467 | MS | 4.45 | 4.12 | 8.18 | 3.34 | 3.83 | 3.18 |
| 5468 | MS | 2.97 | 4.81 | 2.98 | 4.77 | 3.27 | 9.22 |
| 5469 | MS | 5.98 | 3.49 | 12.13 | 6.41 | 4.21 | 6.56 |
| 5470 | MS | 3.74 | 1.91 | 2.56 | 4.03 | 2.43 | 3.65 |
| 5474 | MS | 2.38 | 1.32 | 8.74 | 1.61 | 1.99 | 1.24 |
| 5476 | MS | 2.90 | 1.90 | 8.02 | 3.17 | 3.05 | 3.42 |
| 5480 | MS | 2.63 | 1.95 | 4.92 | 3.44 | 2.86 | 6.04 |
| 5482 | MS | 3.15 | 2.27 | 1.68 | 1.99 | 2.67 | 2.29 |
| 5483 | MS | 6.70 | 5.78 | 5.27 | 6.72 | 9.71 | 5.43 |
| 5484 | MS | 3.57 | 2.92 | 6.31 | 5.50 | 3.56 | 3.57 |
| 5485 | MS | 8.44 | 3.22 | 6.95 | 3.52 | 3.36 | 6.29 |
| 5486 | MS | 3.72 | 3.93 | 14.71 | 3.60 | 2.90 | 2.70 |
| 5489 | MS | 1.96 | 1.23 | 2.37 | 1.54 | 1.23 | 1.38 |
| 9999 | MS | 3.46 | 2.79 | 1.86 | 2.84 | 2.00 | 3.46 |
| 5184 | OND | 2.47 | 1.06 | 3.08 | 2.25 | 1.47 | 1.91 |
| 5185 | OND | 0.97 | 0.81 | 1.39 | 0.88 | 1.01 | 0.80 |
| 5186 | OND | 1.67 | 2.09 | 2.69 | 3.29 | 2.03 | 1.12 |
| 5187 | OND | 1.55 | 1.82 | 2.61 | 1.41 | 1.40 | 1.24 |
| 5188 | OND | 6.94 | 1.99 | 2.77 | 2.01 | 1.74 | 1.82 |
| 5190 | OND | 1.02 | 0.61 | 0.70 | 1.13 | 1.13 | 0.73 |
| 5191 | OND | 1.10 | 0.77 | 2.20 | 1.74 | 1.32 | 1.00 |
| 5192 | OND | 0.86 | 0.98 | 1.71 | 1.73 | 1.47 | 0.92 |
| 5193 | OND | 1.62 | 1.25 | 1.31 | 0.83 | 0.76 | 0.79 |
| 5194 | OND | 2.25 | 1.40 | 2.22 | 1.43 | 1.89 | 1.29 |
| 5195 | OND | 3.58 | 2.69 | 4.77 | 2.63 | 1.90 | 2.00 |
| 5196 | OND | 1.85 | 1.60 | 4.68 | 1.62 | 1.15 | 2.30 |
| 5197 | OND | 2.18 | 0.98 | 0.87 | 1.78 | 1.67 | 1.09 |
| 5198 | OND | 2.01 | 1.82 | 2.16 | 2.62 | 2.45 | 1.28 |
| 5199 | OND | 1.36 | 1.27 | 0.88 | 1.21 | 0.90 | 0.92 |
| 5224 | OND | 1.02 | 1.01 | 0.96 | 1.17 | 1.54 | 0.94 |
| 5225 | OND |  |  |  |  |  |  |
| 5226 | OND | 1.63 | 1.50 | 1.34 | 2.22 | 1.58 | 0.92 |
| 5233 | OND | 2.07 | 0.91 | 0.94 | 3.43 |  | 1.31 |
| 5234 | OND | 0.83 | 0.69 | 1.41 | 1.30 | 2.46 | 1.02 |
| 5235 | OND | 1.66 | 2.08 | 1.91 | 1.64 | 1.31 | 1.59 |
| 5236 | OND | 2.64 | 1.57 | 2.92 | 2.32 | 2.89 | 1.52 |

TABLE 2-continued

| Patient I.D | Disease | Ga4Ga | Ga | GNa | Ga2Ga | Ga3Ga | Ga6-Ga |
|---|---|---|---|---|---|---|---|
| 5237 | OND | 3.98 | 2.09 | | | | 2.90 |
| 5239 | OND | | 2.03 | 1.62 | 1.35 | 1.15 | 2.38 |
| 5244 | OND | 1.45 | 1.05 | 1.63 | 1.34 | 1.41 | 1.11 |
| 5400 | OND | 1.20 | 0.76 | 1.42 | 1.58 | 1.72 | 1.27 |
| 5401 | OND | 1.87 | 1.26 | 2.26 | 2.41 | 2.22 | 1.03 |
| 5402 | OND | | | 3.57 | 2.01 | 2.29 | |
| 5404 | OND | 1.66 | 1.23 | 1.70 | 1.67 | 1.72 | 1.31 |
| 5405 | OND | 1.61 | 0.78 | 1.65 | 1.31 | 1.48 | 1.09 |
| 5406 | OND | 1.22 | 1.13 | 1.20 | 1.48 | 1.39 | 1.15 |
| 5407 | OND | 2.56 | 1.86 | 4.59 | 2.92 | 2.41 | 2.45 |
| 5408 | OND | | | 2.70 | | | |
| 5706 | OND | 1.56 | 1.07 | 2.39 | 2.05 | 1.53 | 1.02 |
| 5707 | OND | 2.30 | 1.42 | 2.37 | 2.05 | 2.06 | 1.40 |
| 5708 | OND | 2.21 | 1.45 | 2.96 | 2.29 | 2.20 | 2.03 |
| 5709 | OND | 2.38 | 1.94 | 2.60 | 2.01 | 2.04 | 2.11 |
| 5710 | OND | 4.22 | 2.55 | 1.87 | 2.47 | 3.33 | |
| 5711 | OND | 1.13 | 0.88 | 0.89 | 1.02 | 1.16 | 0.99 |
| 5712 | OND | 0.83 | 0.93 | 1.25 | 1.25 | 1.14 | 0.66 |
| 5719 | OND | 2.29 | 2.21 | 2.99 | 3.26 | 3.29 | 1.73 |
| 5720 | OND | 1.22 | 1.39 | 1.25 | 2.58 | 2.12 | 1.45 |
| 5721 | OND | 1.74 | 1.02 | 1.11 | 1.46 | 1.92 | 1.45 |
| 5725 | OND | 1.90 | 1.81 | 1.60 | 2.12 | 2.23 | 2.16 |
| 5726 | OND | | | | | | |
| 5727 | OND | | | | | | |
| 5728 | OND | 1.28 | 0.93 | 1.38 | 1.54 | 1.26 | 0.98 |
| 5729 | OND | 2.85 | 0.98 | 2.96 | 1.69 | 1.73 | 1.97 |
| 5730 | OND | 1.50 | 1.18 | 1.59 | 1.56 | 1.89 | 1.13 |
| 5731 | OND | 2.01 | 1.66 | 1.57 | 2.05 | 2.24 | 1.88 |
| 5732 | OND | 1.65 | 1.37 | 2.20 | 3.20 | 2.79 | 1.31 |
| 5733 | OND | 4.02 | 2.51 | 4.41 | | 2.78 | 1.35 |
| 5734 | OND | 1.38 | 1.05 | 1.55 | 1.29 | 1.19 | 1.29 |
| 5737 | OND | 1.83 | 1.76 | 4.04 | 2.38 | 1.98 | 1.56 |
| 5739 | OND | 2.56 | 1.91 | 3.92 | 3.14 | 3.30 | 2.25 |
| 5740 | OND | 2.16 | 1.59 | 3.26 | 2.13 | 1.81 | 2.29 |
| 5741 | OND | 2.26 | 1.54 | 2.71 | 1.77 | 2.53 | 3.29 |
| 6102 | OND | 4.96 | | | | | |
| 8189 | OND | 1.76 | 1.16 | 2.33 | 1.82 | 1.79 | 1.51 |
| 8191 | OND | 1.62 | 1.57 | 2.79 | 3.87 | 3.06 | 2.22 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of differentiating between multiple sclerosis (MS) and other neurological diseases (OND) in a subject, the method comprising:
   providing a blood sample from a subject;
   detecting in said blood sample an antibody selected from the group consisting of an IgM type anti-Glc($\alpha$1,2)Glc($\alpha$) antibody, an IgM type anti-Glc($\alpha$1,3)Glc($\alpha$) antibody and an IgM type anti-Glc($\alpha$1,6)Glc($\alpha$)
   comparing the levels of said antibody in said blood sample to levels of said antibody in individuals with OND; and
   differentiating MS from OND in said subject by detection of an elevated level of said antibody in said blood sample compared to an OND level of said antibody.

2. The method of claim 1, wherein said antibody is an anti-Glc($\alpha$1,2)Glc($\alpha$) antibody.

3. The method of claim 1, wherein said antibody is an anti-Glc($\alpha$1,3)Glc($\alpha$) antibody.

4. The method of claim 1, wherein said antibody is an anti-Glc($\alpha$1,6)Glc($\alpha$) antibody.

5. The method of claim 1, wherein said subject is a female.

6. The method of claim 1, wherein said subject is a male.

7. The method of claim 1, wherein said method comprises detecting at least two of said antibodies.

8. The method of claim 1, wherein said method comprises detecting three of said antibodies.

9. The method of claim 1, wherein said MS is relapsing - remitting (RR) MS.

* * * * *

UNITED STATES PATENT AND TRADEMARK OFFICE
CERTIFICATE OF CORRECTION

PATENT NO.        : 7,572,592 B2
APPLICATION NO.   : 11/047124
DATED             : August 11, 2009
INVENTOR(S)       : Dotan et al.

Page 1 of 1

It is certified that error appears in the above-identified patent and that said Letters Patent is hereby corrected as shown below:

The claims:

Column 16, line 20, claim 1, the phrase "body and an IgM type anti-Glc($\alpha$1,6)Glc($\alpha$)" should read -- body and an IgM type anti-Glc($\alpha$1,6)Glc($\alpha$) antibody --.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,572,592 B2 |
| APPLICATION NO. | : 11/047124 |
| DATED | : August 11, 2009 |
| INVENTOR(S) | : Nir Dotan |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (304) days Delete the phrase "by 304 days" and insert -- by 749 days --

Signed and Sealed this

Fourth Day of May, 2010

David J. Kappos
*Director of the United States Patent and Trademark Office*